United States Patent [19]
Viart

[11] Patent Number: 5,879,351
[45] Date of Patent: Mar. 9, 1999

[54] SPINAL OSTEOSYNTHESIS DEVICE ADAPTABLE TO DIFFERENCES OF ALIGNMENT, ANGULATION AND DEPTH OF PENETRATION OF PEDICLE SCREWS

[75] Inventor: Guy Viart, Saint Leger, France

[73] Assignee: Eurosurgical, Beaurains, France

[21] Appl. No.: 65,517

[22] Filed: Apr. 24, 1998

[30] Foreign Application Priority Data

Apr. 3, 1998 [FR] France .................................. 98 04187

[51] Int. Cl.$^6$ ................................................. A61B 17/70
[52] U.S. Cl. ............................................................. 606/61
[58] Field of Search ................................. 606/61, 60, 72, 606/73; 623/17

[56] References Cited

U.S. PATENT DOCUMENTS 5,129,900  7/1992  Asher et al. ............................... 606/61
5,582,612  12/1996  Lin ............................................. 606/61
5,609,592  3/1997  Brumfield et al. ........................ 606/61
5,741,255  4/1998  Krag et al. ................................ 606/61

*Primary Examiner*—Guy V. Tucker
*Attorney, Agent, or Firm*—Young & Thompson

[57] ABSTRACT

The device comprises at least one vertebral rod (2), pedicle screws (3), and connectors (1) interconnecting the rod and the screws. The connectors (1, 10) define an oblong opening (5) extending transversely of the rod and passed through by the screw. The intermediate connectors (1) are made of a malleable plastically deformable material having a capacity of elongation of at least about 20%. The intermediate anchorages of the instrumentation are provided with such connectors (1) which are plastically deformable in their branches (4) passed through by the screw by the effect of the tightening of nuts (8) on the screws when placing the device in position and undeformable by the effect of the bending moments transmitted by the spine in vivo at values lower than 4.5 N.m. The chosen material may be for example pure titanium and its plasticity enables the surgeons to easily adapt the connectors to the differences of alignment, angulation and depth of penetration of the pedicle screws. The connector according to the invention considerably facilitates the mounting of the instrumentations by the surgeon.

6 Claims, 3 Drawing Sheets

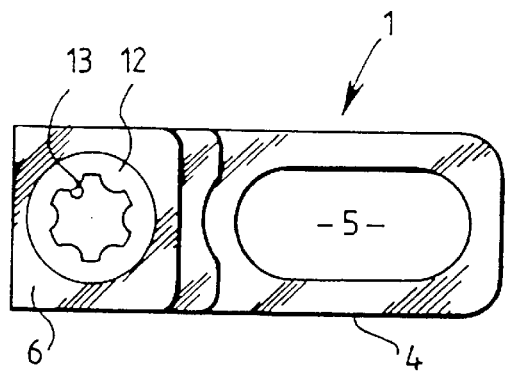
FIG. 1
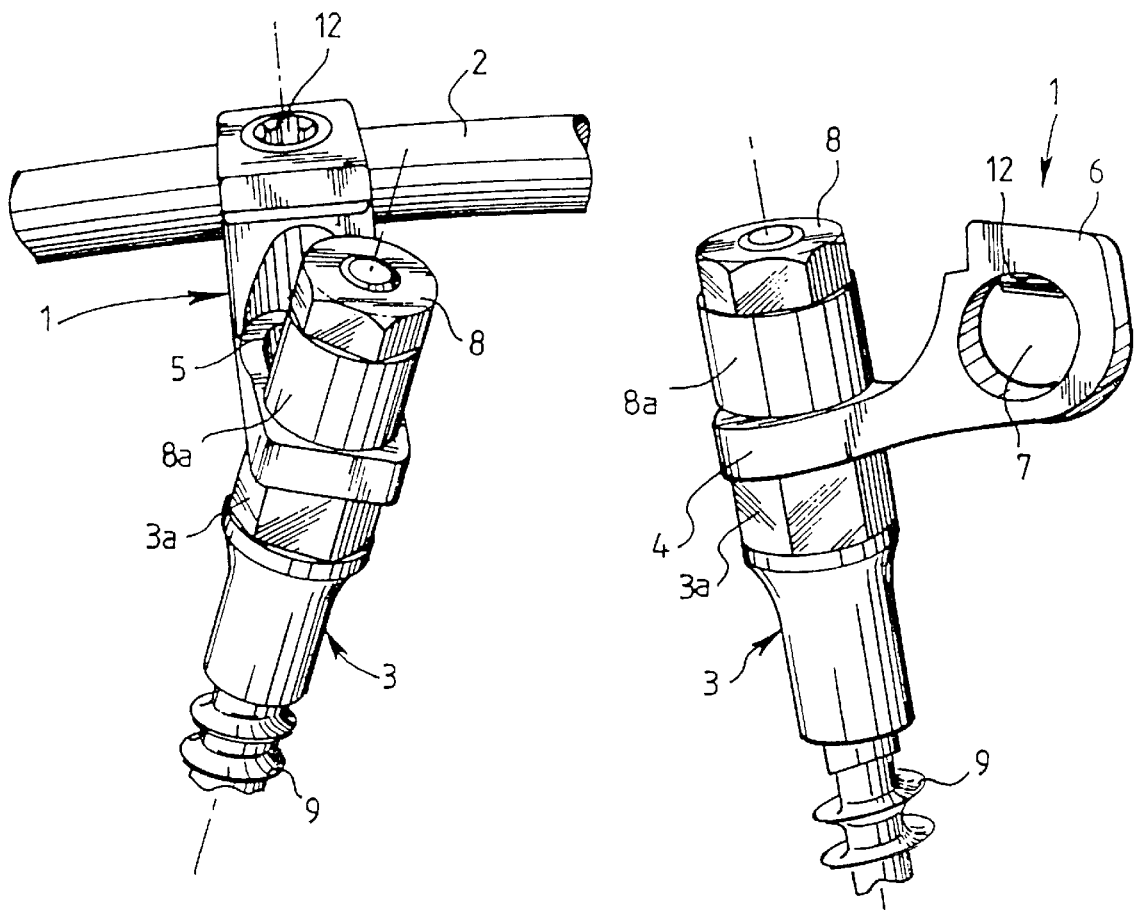
FIG. 2
FIG. 3

SPINAL OSTEOSYNTHESIS DEVICE ADAPTABLE TO DIFFERENCES OF ALIGNMENT, ANGULATION AND DEPTH OF PENETRATION OF PEDICLE SCREWS

The present invention relates to a spinal osteosynthesis device comprising at least one vertebral rod, pedicle screws and connectors which interconnect the rod and the screws and comprise two parts respectively passed through by the screw and by the rod.

A problem when mounting such spinal instrumentations is their adaptation to the differences of alignment, angulation and depth of penetration of the pedicle screws. Most presently known spinal instrumentations of this type are in fact very difficult to adapt to these differences of implantation. When they are adaptable, they are only partly so and consequently cannot cope with all the variations in these parameters. Existing instrumentations are furthermore usually complex owing to the large number of parts and oblige the surgeons to choose appropriate connectors for adapting them to disalignments of the pedicle screws. Further, if the pedicle screws have different depths of anchorage from one screw to the other, adaptation to these differences is difficult; the surgeon tightens screws which are then liable to be wrenched away. Finally, the clamping of certain screws on their connectors is sometimes unsatisfactory owing to these disalignments and differences in the anchorage depth, which complicated measures taken by the surgeon do not always compensate.

Placing existing instrumentations in position is also rendered delicate by the use of the pedicle aiming method; according to this method, the surgeon draws an imaginary line through the different theoretical places of implantation of the screws connecting the pedicles, then aims in each of the sectors at the places for the screws. In fact, some surgeons unspecialized in spinal surgery choose to aim at the middle of each sector, which does not necessarily correspond to the best alignment of the screws.

Further, "polyaxial" pedicle screws are known which permit an adaptation to differences in the angulation of the pedicle screws, but a difficult adaptation in alignment and an even more difficult adaptation in depth.

A spinal instrumentation is also known having connectors which define an oblong opening extending transversely of the rod for receiving pedicle screws. These connectors permit the adaptation of the screws in alignment but not in angulation and in depth without the use of special washers. Such a device requires the measurement, the selection and the positioning of washers, which are generally delicate operations. Further, the multiplicity of the interposed elements increases the risk of failure of the fixation.

An object of invention is to provide a device of the aforementioned type comprising screw-rod connectors permitting an automatic and easy adaptability to the differences in the positioning of the pedicle screws in alignment, angulation and depth.

According to the invention, the connectors comprise an oblong opening extending transversely of the rod and adapted to be passed through by the associated screw, and at least one connector is made of a malleable material, plastically deformable in its part passed through by the screw by the effect of the tightening of a nut on the screw when it is placed in position, and undeformable by the effect of the bending moments transmitted by the spine in vivo, the values of which are lower than about 4.5 N.m.

The chosen material therefore has a great plastic capacity corresponding to a capacity of elongation of at least about 20% beyond a stress of 275 MPa. This permits producing, by a mere tightening of the nuts fixing the pedicle screws on the connectors, the plastic deformation necessary for the adaptation of the connectors to the different pedicle screws and to the rod interconnecting them. In this way the operational manipulation by the surgeon for placing the osteosynthesis material in position in arthrodesis of the spine is considerably facilitated.

By way of a non-limitative example, the connector may be composed of pure titanium, for example of grade ISO 5832-2, which becomes malleable and plastically deformable beyond a force of 53 daN exerted by the tool tightening the nut fixing the screw to the corresponding connector.

In a preferred embodiment of the device according to the invention, only the intermediate connectors are made of a plastically deformable material, while the end connectors are undeformable by the forces they are subjected to when they are being placed in position and subsequently by the forces resulting from the movements of the patient.

Further features and advantages of the invention will be apparent from the following description with reference to the accompanying drawings which illustrate an embodiment of the invention by way of a non-limitative example.

BREIF DESCRIPTION OF THE DRAWINGS

FIG. 1 is a top plan view, to an enlarged scale, of an embodiment of the connector of the spinal osteosynthesis device to which the invention relates.

FIG. 2 is a partial perspective view, to an enlarged scale, of a spinal osteosynthesis device provided with a connector conforming to FIG. 1 which adapts itself by a plastic deformation to an effective connection of the rod to the pedicle screw.

FIG. 3 is a partial perspective view at another angle of the device of FIG. 2.

DETAILED DESCRIPTION OF THE INVENTION

Figure 4:
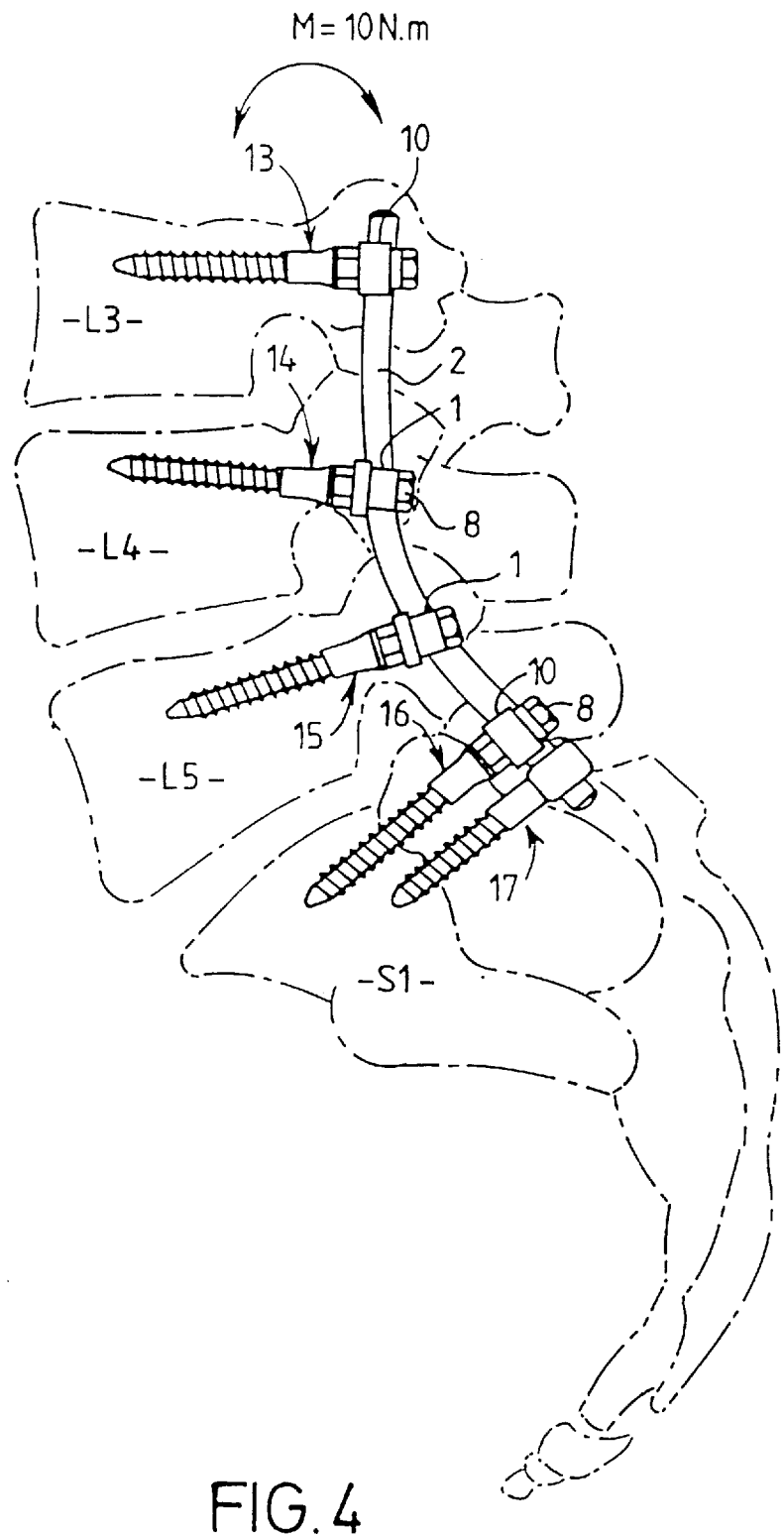
FIG. 4 is a side elevational view, to a reduced scale, of a spinal osteosynthesis device according to the invention placed in position on a corresponding spinal segment.

Shown in FIGS. 1 to 3 is a connector 1 for interconnecting a vertebral rod 2 and a pedicle bone anchorage screw 3 of a spinal osteosynthesis device.

The connector 1 has a substantially L-shaped profile in the large branch 4 of which there is provided an oblong opening 5 adapted to be passed through by the associated screw 3, with a freedom of positioning of the screw in this opening 5 in the direction transverse to the rod 2.

Provided in the small branch 6 of the connector 1 is an opening 7 for the passage of the rod 2. The pedicle screw 3 may be clamped in the required position on the connector 1 by means of a nut 8 having a cylindrical base 8a screwed on the threaded end portion of the screw 3 projecting from the connector 1. The branch 4 of the connector 1 is interposed between the hexagon head 3a and the cylindrical base 8a of the nut 8 mounted on the rod. The rod 2 may be clamped in the branch 6 by means of a screw 12 which has a socket 13 for engagement of a screwing tool and is screwed in a tapped hole in the branch 6.

The connector 1 is made of a malleable, plastically deformable, material having a capacity of elongation of about 20%. The material is chosen to be plastically deformable by a force F of at least 53 daN, which corresponds to a bending moment of 4.5 N.m exerted on the bone anchorage screw 3.

Such a material having a large plastic capacity permits, by the mere tightening of the nuts 8 fixing the screws 3 to the attachments formed by the connectors 1, producing in the branches 4, passed through by the screws 3, by means of the bending force F exerted on these branches 4, the plastic deformation necessary for the adaptation of the different pedicle screws and of the rod 2 interconnecting them, to the particular anatomy of the considered spinal segments. Indeed, this possibility of plastic deformation within the range of the tightening and torsional forces F (FIG. 6) exerted by the surgeon on the connector 1 permits suitably deforming the latter, for example as shown in FIGS. 2 and 3, for adapting it to the differences in alignment, angulation and depth of penetration of the bone anchorage screws 3. The branch 4 of the connector 1 is plastically deformable by tightening the nut 8 on the screw 3 when it is placed in position, but undeformable by the effect of the bending moments transmitted by the spine in vivo the values of which are lower than about 4.5 N.m.

The pure titanium of grade ISO 5832-2 of the connector 1 does not exhibit after deformation the phenomenon of excessive work-hardening and therefore fracture initiation. This material is very ductile and capable of undergoing torsion.

A possible second material is stainless steel 316L used "annealed" which has high ductility properties.

The design of this connector 1 was made possible by the observation and biomechanical analysis of multisegmental pedicle fixations in the treatment of spinal pathologies. The biomechanical behaviour of the spine provided with an instrumentation employing a multisegmental fixation with pedicle screws was analyzed on a tri-dimensional mathematical model by finished elements. This analysis revealed large differences in stresses in the region of each vertebra. Indeed, this biomechanical analysis carried out on a spinal instrumentation such as that of FIGS. 4 and 5, permitted measuring the stresses to which the bone anchorage elements are subjected at different levels of the segment.

Figures 5, 6:
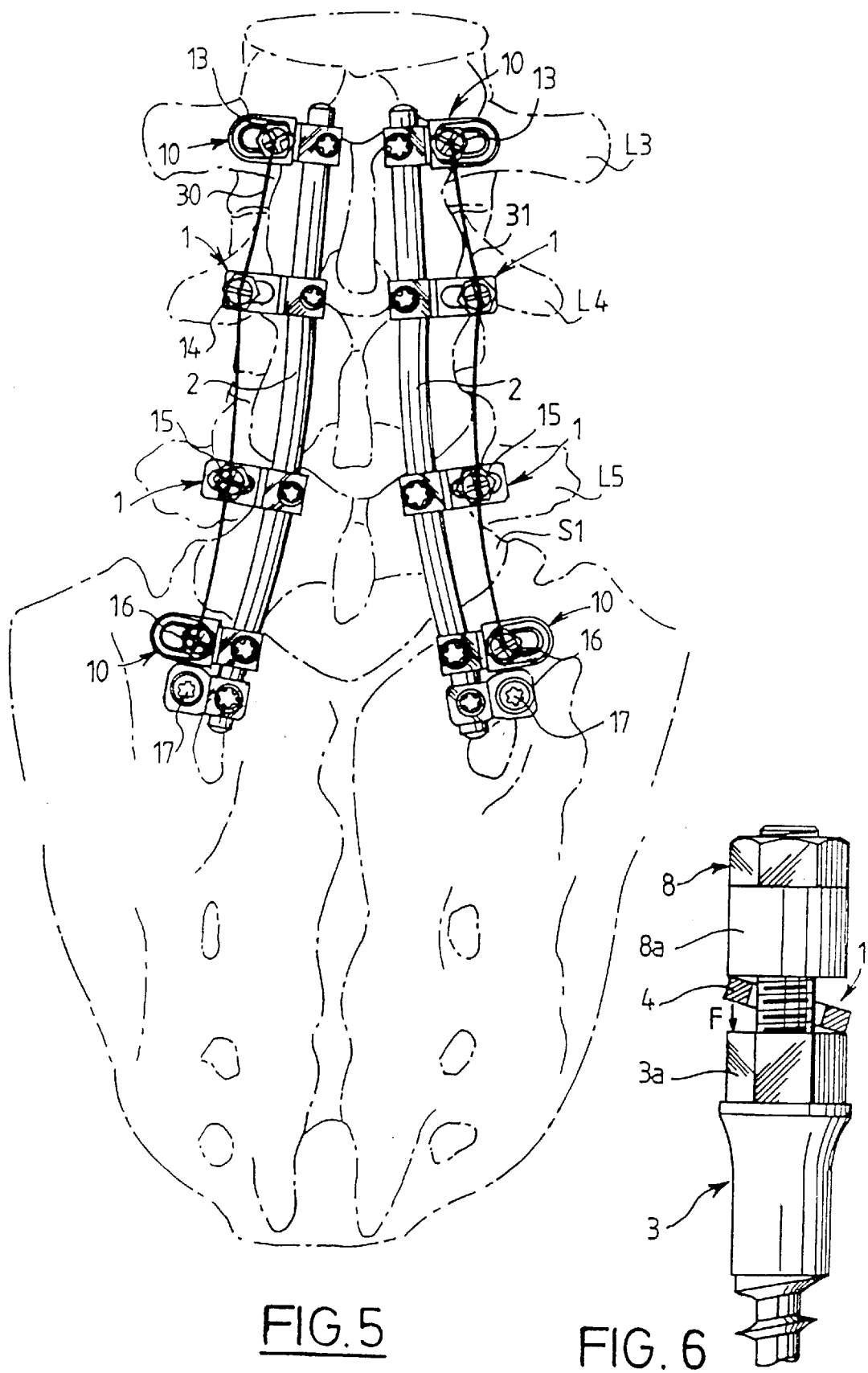
FIG. 5 is a rear elevational view of the device of FIG. 4.
FIG. 6 is a partial side elevational view of a device according to FIGS. 2 and 3 at the beginning of the stage in which the nut is tightened on the screw and the connector.

The instrumentation of FIGS. 4 and 5 comprises two lumbo-sacral vertebral rods 2 extending along the three lumbar vertebrae L3, L4, L5 and the sacrum S1. Associated with each rod 2 are three pedicle screws 13, 14, 15 respectively anchored in the lumbar vertebrae L3, L4, L5, while two screws 16, 17 are anchored in the sacrum S1. These different screws 13 . . . 17 undergo variations in alignment corresponding to the lines 30, 31 through the respective screws of each rod 2. The biomechanical analysis of a load on the spine in bending at 10 N.m permitted measuring the bending moments M exerted on the respective screws: at L3 this moment M was 1 N.m, at L4 0.08 N.m, at L5 0.3 N.m and at S1 0.6 N.m.

It is therefore clear that the stresses on the intermediate anchorages 14, 15 are very distinctly lower than those of the ends 13, 16, 17. Consequently, the intermediate pedicle screws 14, 15 and their systems of connection 1 with the rod 2 on the intermediate vertebrae L4, L5 are little stressed.

The connector 1 according to the invention was therefore designed by taking into account these low stresses for the intermediate anchorages so as to provide surgeons with new possibilities resulting in a greater versatility and an increased simplicity in the mounting of spinal arthrodesis fixations. Indeed, the malleable and plastically deformable connector 1 provided by the invention has the feature of being adaptable to any positioning of the pedicle screws while permitting an effective fixation without impairing the bone anchorage.

The connectors 1 according to the invention are used solely for the intermediate anchorages of an instrumentation, for example, the screws 14, 15 on the assembly shown in FIGS. 4 and 5. On the other hand, the end anchorages (screws 13, 16, 17) are associated with connectors 10 which have the same structure as the connectors 1, in particular the oblong opening 5, but are undeformable within the range of the bending and tightening forces exerted by the surgeon and the range of the bending forces to which these anchorage elements are subjected once placed on the patient, ie. higher than 8 N.m. The connectors 10 may be for example composed of a titanium alloy.

The intermediate connectors 1 plastically adapt themselves to the differences of angulation and level of the pedicle screws, with no stress on the bone anchorage elements in respect of both bending and wrenching. There is consequently a simplification and a facilitation of the mounting of the instrumentation which are very appreciable for surgeons as compared with known prior instrumentations. Indeed, in respect of these intermediate anchorages, it is sufficient for the surgeons to subject the connectors 1 to the required torsions to adapt them to each local anatomy. After this plastic deformation, the intermediate connectors 1 are no longer deformed since the low stresses at these different places are insufficient to cause their subsequent deformation.

Generally, the osteosynthesis device according to the invention is provided with at least one malleable and plastically deformable connector 1.

What is claimed is:

1. Spinal osteosynthesis device comprising at least one vertebral rod, pedicle screws, connectors interconnecting said at least one rod and said pedicle screws, each connector comprising a first part and a second part respectively passed through by the respective pedicle screw and by said at least one rod, each connector comprising in said first part an oblong opening extending transversely of said at least one rod and adapted to be passed through by the respective pedicle screw, at least one of said connectors being made of a malleable material plastically deformable in said first part by the effect of the tightening of a nut on the respective pedicle screw when it is placed in position, and said at least one connector being undeformable by the effect of bending moments transmitted by the spine in vivo, the values of which are lower than about 4.5 N.m.

2. Device according to claim 1, wherein said malleable material has a capacity of elongation of at least 20%.

3. Device according to claim 1, wherein said connectors comprise end connectors fixed to said at least one rod adjacent to ends thereof and intermediate connectors between said end connectors, said intermediate connectors being made of said malleable plastically deformable material in said first parts thereof, and said end connectors being made of an undeformable material.

4. Device according to claim 1, wherein said malleable material of said at least one connector is pure titanium.

5. Device according to claim 1, wherein said malleable material of said at least one connector is an annealed stainless steel having high ductility properties.

6. Connector for a spinal osteosynthesis device comprising a vertebral rod, pedicle screws, and connecting means for interconnecting said rod and said screws, said connector being intended to be part of said connecting means and comprising a first part and a second part, an oblong opening in said first part for receiving a respective one of said pedicle screws and adapted to extend transversely of said rod in said device, a second opening in said second part for receiving said rod, said connector being made of a malleable material plastically deformable in said first part by the effect of the tightening of a nut on said respective pedicle screw when it is placed in position, and said connector being undeformable by the effect of bending moments transmitted by the spine in vivo, the values of which are lower than about 4.5 N.m.

* * * * *